United States Patent [19]

Gallay et al.

[11] 4,035,423

[45] July 12, 1977

[54] PROCESS FOR THE PREPARATION OF 3,4-DIALKOXYANILINES

[75] Inventors: Jean-Jacques Gallay, Magden; Ernst Aufderhaar, Kaiseraugst; Peter Labuhn, Birsfelden, all of Switzerland

[73] Assignee: Ciba-Geigy Corporation, Ardsley, N.Y.

[21] Appl. No.: 659,818

[22] Filed: Feb. 20, 1976

Related U.S. Application Data

[63] Continuation-in-part of Ser. No. 484,048, June 28, 1974, abandoned.

[30] Foreign Application Priority Data

July 3, 1973 Switzerland .................. 9669/73

[51] Int. Cl.$^2$ .................................. C07C 93/14
[52] U.S. Cl. .................... 260/571; 260/206; 260/575
[58] Field of Search .................. 260/571, 575, 206

[56] References Cited

U.S. PATENT DOCUMENTS

| | | | |
|---|---|---|---|
| 1,564,214 | 12/1925 | Derick et al. | 260/575 |
| 1,722,417 | 7/1929 | Grether | 260/575 |
| 1,890,430 | 12/1932 | Perkins et al. | 260/571 |
| 2,191,040 | 2/1940 | McNally et al. | 260/206 X |
| 3,883,503 | 5/1975 | Assche et al. | 260/206 |

OTHER PUBLICATIONS

Klarmann et al., "J. Amer. Chem. Soc", vol. 54, pp. 1204–1211 (1932).
Colour Index, Third Edition, vol. 4, p. 4064, C.I. 14260.

*Primary Examiner*—Daniel E. Wyman
*Assistant Examiner*—John J. Doll
*Attorney, Agent, or Firm*—Frederick H. Rabin

[57] ABSTRACT

A new process for the production of 3,4-dialkoxyanilines in which the two alkyl groups are different from each other is disclosed. The process comprises the stepwise introduction of the alkyl groups in different stages of the process by converting pyrocatechol into its monoalkyl ether, coupling said monoalkyl ether with a phenyldiazonium salt, alkylating the 3-alkoxy-4-hydroxy-azobenzene obtained to form 3,4-dialkoxyazobenzene and reductively cleaving the latter to the corresponding 3,4-dialkoxyaniline. The 3,4-dialkoxyanilines obtainable by the new process are valuable intermediates for the preparation of 4-hydroxy-6,7-dialkoxy-3-quinoline carboxylic acid esters which are excellent coccidiostats.

10 Claims, No Drawings

PROCESS FOR THE PREPARATION OF 3,4-DIALKOXYANILINES

CROSS-REFERENCE TO RELATED APPLICATIONS

This application is a continuation-in-part of application Ser. No. 484,048 filed June 28, 1974, now abandoned.

The present invention relates to a process for the production of 3,4-dialkoxyanilines of formula I

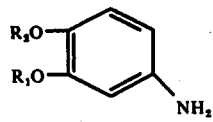
(I)

wherein (a) $R_1$ and $R_2$ are different from each other and each of $R_1$ and $R_2$ represents a member of the group consisting of $C_1$–$C_{20}$ alkyl and $C_3$–$C_6$ cycloalkyl $C_1$–$C_4$ alkyl (b) or $R_1$ is a $C_1$–$C_4$ alkyl group and $R_2$ is a $C_8$–$C_{10}$ alkyl group.

Among the compounds of formula I those are preferred wherein one of the groups $R_1$ and $R_2$ is a $C_8$–$C_{16}$ alkyl group while the other is a $C_3$–$C_6$ cycloalkyl $C_1$–$C_4$ alkyl group. Other preferred compounds of formula I are those wherein $R_1$ is a $C_1$–$C_4$ alkyl group and $R_2$ is a $C_8$–$C_{10}$ alkyl group. The specific preferred compounds of formula I are 3-n-decyloxy-4-cyclopropylmethoxyaniline and 3-ethoxy-4-n-decyloxyaniline.

Compounds of formula I are valuable intermediates for the preparation of 4-hydroxy-6,7-dialkoxy-3-quinoline carboxylic acid esters of the formula

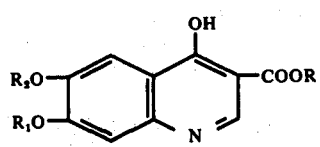

wherein R is a lower alkyl group and $R_1$ and $R_2$ have the meaning given above. These compounds are excellent coccidiostats. In this connection reference is made to U.S. Pat. Nos. 3,485,845 and 3,496,184 wherein such compounds, their preparation and their coccidiostatic action is described in detail.

According to a method described in U.S. pat. No. 3,485,845 3,4-dialkoxyanilines of formula I are prepared by converting pyrocatechol into its dialkylether, introducing a nitro group into the 4-position, selectively hydrolysing the 1-alkoxy group of the 1,2-dialkoxy-4-nitrobenzene formed to obtain 3-alkoxy-4-hydroxy-nitrobenzene which is realkylated and subsequently reduced to obtain the desired 3,4-dialkoxyaniline containing different alkyl groups from pyrocatechol in a five step process.

According to a further method described in U.S. Pat. No. 3,485,845 3,4-dialkoxyanilines of formula I are prepared by alkylating the monosodium salt of 4-nitro-pyrocatechol to obtain a 2-alkoxy-5-nitro-phenol which is converted in a further alkylation step into a 3,4-dialkoxy-nitrobenzene which in turn is reduced to form the desired 3,4-dialkoxyaniline formula I. Since the 4-nitro pyrocatechol used as starting material has to be prepared by bis-alkylation or bis-acylation of pyrocatechol, nitration of the pyrocatechol diether or diester obtained and subsequent hydrolysis of the 4-nitropyrocatechol diether or diester the 3,4-dialkoxyanilines of formula I are obtained from pyrocatechol in a six step process. Further, according to a method described in U.S. Pat. No. 3,496,184 the 3,4-dialkoxyanilines of formula I can be prepared by monoalkylation of pyrocatechol followed by acylation, for example with benzoylchloride, to form a 2-alkoxy-phenylester, subsequent nitration of said 2-alkoxy-phenylester to form a 2-alkoxy-5-nitro-phenyl ester, hydrolysis of the latter to obtain a 3-hydroxy-4-alkoxy-nitrobenzene which is alkylated to form a 3,4-dialkoxynitrobenzene which is reduced to the desired 3,4-dialkoxyanilines. According to this method the 3,4-dialkoxyanilines of formula can be obtaned in a six step process.

The methods known from the prior art referred to above are disadvantageous in several respects. Thus, known processes are very complicated because a large number of steps is necessary to produce the desired products. The large number of reaction steps detrimentally affects the yield of the final products. This is particularly true with respect to the nitration which is involved in each of the known methods.

Therefore, it is the object of the present invention to avoid the disadvantages inherent to the prior art methods and to provide a simplified process according to which the intermediates of formula I can be obtained in better yields than in the known processes while the number of reaction steps is reduced. According to the present invention the 3,4-dialkoxyanilines of formula I are produced by reacting pyrocatechol with a reactive ester of an alcohol derived from the group $R_1$ as defined above, to form the monoalkyl ether of the formula II

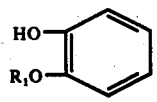
(II)

which is reacted with a phenyl diazonium salt to give an azobenzene of formula III

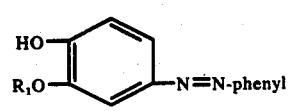
(III)

which is reacted with a reactive ester of an alcohol derived from the group $R_2$, as defined above to form a 3,4-dialkoxyazobenzene of formula IV

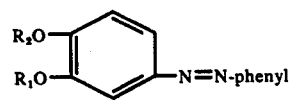
(IV)

and this 3,4-dialkoxy azobenzene is then reductively split to a 3,4-dialkoxyaniline of formula I.

The conversion of pyrocatechol into its monoalkyl ether of formula II can advantageously be performed according to methods described in Houben-Weyl VI 13, p. 49 and following, J. Am. Chem. Soc. 54 (1932) 298–305, dt. 54 (1932) p. 1204 and following, J. Chem. Soc. Japan 72 (1952) p. 546 and following.

According to a preferred embodiment, pyrocatechol is reacted with a compound of formula $R_1X$, by which is meant corresponding halides, sulphuric acid esters and sulphonic acid esters, in the presence of a base, in a solvent or diluent inert to the reactants. Suitable bases are preferably; hydrides, carbonates, oxides, hydroxides or alcoholates of alkali metals and alkaline-earth metals. Used as solvents or diluents inert to the reactants are, for example: water, lower and higher alocohols, lower and higher ketones, open-chain and cyclic ethers or aromatic hydrocarbons. For the preparation of pyrocatechol monoalkylethers of formula II, it is advantageous to operate with an excess of pyrocatechol exceeding the molar ratio of 1:1, this can be recovered by suitable methods after the reaction. It is advantageous to employ a molar ratio of 2:1 to 4:1. Pyrocatecholmonoalkyl ethers of formula II are then reacted with a suitable diazonium salt to obtain azobenzenes of formula III. The substituent "phenyl" in formula III is merely given as an example of the preferably used aniline; it is of course possible to use also diazonium salts of substituted anilines, such as, e.g. of toluidine, of sulphanilic acid, etc.. Suitable phenyldiazonium salts are essentially all diazonium salts capable of coupling which are known from the literature. Especially suitable are diazonium salts of which the coupling products offer preparative advantages in the carrying out of the overall synthesis according to the invention. These advantages can be that few or no by-products are formed; that the reaction products can be easily isolated, e.g. by virtue of their difficult solubility in the employed solvent; or that, after reductive splitting, readily separable phenylamines are formed. Water is most suitable as the reaction medium; but also organic solvents may be used. If water is employed, then it is advantageous to operate in the neutral to alkaline pH-range. The reaction temperature is between −20° and +50° C, preferably between −10° and +10° C. The most favourable molar ratio of the reactants is 1:1; however, deviations of up to 20 mol-% can also lead to good results being obtained. In the course of the overall synthesis according to the invention, it is possible, and, depending on the consequent reaction, in certain cases advantageous to continue processing the reaction mixture from the coupling reaction without further preparation; the reaction products, however, can also be separated and purified, e.g. by crystallisation or chromatography. The alkylation of the azobenzenes of formula III is performed by reacting said azobenzenes with a compound of the formula $R_2X$ by which is meant corresponding halides, sulphuric acid esters and sulphonic acid esters, in the presence of a base, in a solvent or diluent inert to the reactants. Suitable bases are preferably hydrides, carbonates oxides, hydroxides or carbonates of alkali metals and alkaline-earth metals. As solvents or diluents inert to the reactants for example water, lower and higher alcohols, lower and higher ketones, open-chain and cyclic ethers, aromatic hydrocarbons or N,N-dialkylformamide, particularly N,N-dimethyl formamide, may be used.

The reductive splitting of the azobenzenes of formula III to the corresponding anilines of formula IV is advantageously performed according to the method described in Houben-Weyl XI/1, from p. 522. Suitable reducing agents are the usually employed reagents, such as sodium dithionite, hydrogen sulphide and salts thereof, sodium bisulphite zinc or tin (II) chloride; however, the reductive splitting is advantageously perform with catalytically activated hydrogen at normal pressure or at elevated pressure. Hydrogenation catalysts may be, for example: Raney-nickel, palladium or platinum, optionally on suitable carriers. Suitable reaction media are, e.g. water, alcohols, dioxane, pyridine, dimethylformamide and methylcellosolve. The temperatures are advantageously between 0° and 50° C.

The working up of the reaction mixture consists essentially in the separation and, optionally, recovery of the arylamine occurring as by-product in the course of the hydrogenating splitting. Separation of arylamine can be effected by distillation (for example, as azeotropic distillation), extraction, fractional crystallisation or chromatography. After separation of the by-products, the further processing of the reaction product can be performed directly without further purification, optionally with use of the solvent system used for the reduction process, or, alternatively, purificaton of the products by crystallisation, dissolving and reprecipitation, distillation or chromatography can be carried out.

The 3,4-dialkoxy anilines of formula I can be further converted into 4-hydroxy-6,7-dialkoxy-3-quinoline carboxylic acid esters according to method described in U.S. Pat. Nos. 3,485,845 and 3,496,184. For this purpose the 3,4-dialkoxyanilines of formula I are first reacted with an alkoxymethylenemalonic acid-dialkyl ester to form a 3,4-dialkoxy-anilinomethylenemalonic acid-dialkylester, which is subsequently thermally cyclised to a 4-hydroxy-6,7-dialkoxy-3-quinoline carboxylic acid ester.

According to the present invention the 3,4-dialkoxyanilines of formula I can be obtained in a process which is considerably less complicated than the previously known processes while the yield of 3,4-dialkoxyanilines of formula I is significantly increased. Thus, according to the present invention the 3,4-dialkoxyanilines of formula I are obtained from pyrocatechol an starting material in a four step process whereas five and six reaction steps are necessary to produce the same compounds according to known methods.

Further, the 3,4-dialkoxyanilines of formula I are obtained according to the invention in a yield of about 70% or more of the theoretical amount calculated on pyrocatechol whereas according to a known method comprising dibenzoylation of pyrocatechol, nitration of the pyrocatechol dibenzoate, hydrolysis 4-nitropyrocatechol dibenzoate, successive introduction of alkyl groups $R_1$ and $R_2$ into 4-nitropyrocatechol and reduction of 3,4-dialkoxy-nitrobenzene the 3,4dialkoxyanilines of formula I are obtained in a yield of less than 50% of the theoretical amount calculated on pyrocatechol.

The following examples serve to illustrate the process according to the invention. Temperature values are expressed in degrees centigrade.

EXAMPLE 1 a. 165 g of pyrocatechol in 400 ml of ethanol is heated with 78 g of ethyliodide under nitrogen to the reflux temperature, and an addition is made in the course of three hours of a solution of 33 g of potassium hydroxide in 70 ml of water. After 5 hours heating at reflux temperature, the reaction mixture is concentrated to dryness. After addition of a solution of 50 g potassium hydroxide in 70 ml of water the mixture is steam distilled in order to remove pyrocatechol diethyl ether formed as by-product and unreacted ethyliodide. Than the resulting aqueous solution is slightly acidified with 6N hydrochloric acid, and again steam-distilled. The crude pyrocatechol monoethyl ether obtained is separated from the aqueous layer, dried and distilled in vacuo. Yield 55 g, b.p. 68° C / 4 Torr.

b. 105 g of aniline is dissolved in 290 ml of conc. hydrochloric acid and 350 ml of water, and the solution is cooled to 0° to 5°. At this temperature, an addition is made dropwise, with stirring, of a solution of 84 g of sodium nitrite in 250 ml of water. After 10 minutes' stirring at 0° to 5°, the diazonium salt solution is rendered neutral with 105 g of sodium bicarbonate, and 48 g of sodium acetate (anhydrous) is added. This solution is added dropwise, with stirring, to a solution, cooled to 0° to 5°, of 138 g of 2-ethoxy-phenol in 4300 ml of ethanol, with the temperature being maintained at 0° to 5°. After four hours' stirring at this temperature the greater part of ethanol becomes distilled off. After stirring of the residue with 2000 ml of water, the product is taken up in chloroform. The chloroform layer is subsequently washed with water, dried by means of magnesium sulphate and concentrated by evaporation. There is obtained 3-ethoxy-4-hydroxy-azobenzene, which, as liquid crude product, is used in the next reaction stage.

c. 24.2 g of 3-ethoxy-4-hydroxy-azobenzene is heated with 4 g of sodium hydroxide (pulverised) and 500 ml of toluene on a water separator until anhydrous solvent distills off. To the reaction mixture are then added 100 ml of dimethylformamide (anhydrous) and 0.5 g of sodium iodide, and the toluene is removed by distillation (internal temperature 130°). After cooling to 80°, 25 g of n-decylbromide is added dropwise, and the mixture is subsequently refluxed for 2 hours. After the mixture has cooled to room temperature, water is added and the whole is repeatedly extracted with toluene. The combined toluene extracts are dried over magnesium sulphate; the solvent is distilled off, and the residue, 3-ethoxy-4-n-decyloxyazobenzene, is taken up, without further purification, in 400 ml of ethanol. 5 g of Raney nickel is added, and hydrogenation is performed at normal pressure until the absorption of hydrogen ceases. After removal of the catalyst, the filtrate is concentrated by evaporation and, after fractional distillation, there is obtained 3-ethoxy-4-n-decyloxy-aniline, B.P. 188°/ 0.005 Torr.

EXAMPLE 2 a. 165 g of pyrocatechol in 400 ml of ethanol is heated with 110.6 g of n-decylbromide under nitrogen to the reflux temperature, and an addition is made in the course of one hour of a solution of 33 g of potassium hydroxide in 70 ml of water. After about 20 hours' heating at reflux temperature, the reaction mixture is concentrated to dryness. The residue is taken up in water, slightly acidified with concentrated hydrochloric acid, and repeatedly extracted with chloroform. After drying and distillation of the extract, the residue is fractionated; the resulting 2-n-decyloxyphenol has the boiling point 124° to 129° / 0.15 torr.

b. 21 g of ailine is dissolved, in a beaker, in 58 ml of concentrated hydrochloric acid and 70 ml of water, and the solution is cooled to 0° to 5°. An addition is made dropwise at this temperature of a solution of 16.8 g of sodium nitrite in 50 ml of water, with stirring being maintained. After 10 minutes' stirring at 0° to 5°, the diazonium salt solution is rendered neutral with 21 g of sodium bicarbonate, and 9.6 g of sodium acetate (anhydrous) is added. This solution is added dropwise with stirring, to the solution, cooled to 0° to 5°, of 50 g of 2-n-decyloxyphenol in 860 ml of ethanol, with the temperature being kept at 0° to 5°. After 4 hours' stirring at this temperature, 500 ml of water is added. The product is taken up in chloroform; the chloroform layer is subsequently washed with water, and dried with magnesium sulphate. After concentration by evaporation, there remains crude 3-n-decyloxy-4-hydroxy-azobenzene (M.P.: 40° to 45°).

c. A suspension of 35.4 g of 3-n-decyloxy-4-hydroxyazobenzene and 4 g of pulverised sodium hydroxide in 500 ml of toluene is heated on a water separator until pure toluene distills over. To the mixture there are then added 100 ml of dimethylformamide (anhydrous) and 0.5 g of sodium iodide. The toluene is removed by distillation from the reaction mixture (internal temperature 130°). At 80° there is subsequently added 11 g of cyclopropylmethyl chloride whilst stirring is maintained. After slow heating to 120°–125°, the mixture is allowed to stand for 2 hours at this temperature. The mixture is then cooled; 300 ml of water is added and the whole is repeatedly extracted with toluene. The combined toluene extracts are dried with magnesium sulphate, and the toluene is distilled off. After recrystallisation from ethanol, there is obtained 3-n-decyloxy-4-cyclopropylmethoxyazobenzene, M.P. 58°–60°.

d. 400 ml of 2N sodium hydroxide solution and a 3% aqueous sodium hyposulphite solution are added to the mixture, heated to 80°, consisting of 40.8 g of 3-n-decyloxy-4-cyclopropylmethoxy-azobenzene in 2500 ml of ethanol. The reaction mixture must be vigorously stirred in order to prevent the formation of two layers. After decolorisation of the reaction mixture, the ethanol is distilled off, and the remaining solution is repeatedly extracted with chloroform. The extracts are dried by means of sodium sulphate, the chloroform is distilled off and the residue is distilled. The resulting 3-n-decyloxy-4-cyclopropylmethoxy-aniline has the boiling point 183°/0.003.

EXAMPLE 3 a. A mixture of 42 g of sulphanilic acid dihydrate, 26.5 g of anhydrous sodium carbonate and 200 ml of water is heated until everything has dissolved, and then cooled to 15°. A solution of 14.8 g of sodium nitrite in 40 ml of water is then added, and the whole reaction mixture is poured into a mixture of 42.5 ml of concentrated hydrochloric acid and 250 g of ice. 50 g of 2-n-decyloxy-phenol (prepared according to Example 2a) is suspended in a warm solution of 44 g of sodium hydroxide in 240 ml of water; the suspension is stirred for one hour and cooled to 5° by the addition of ice. There is then added, with stirring, the previously prepared sulphanilic acid/diazonium salt suspension; stirring is maintained for a further one to two hours at 20°–30°, and the mixture is acidified with 80 ml of concentrated hydrochloric acid. After 20 minutes' stirring, filtration is performed and the precipitate is dried at 80°. The result is crude 3-n-decyloxy-4-hydroxy-azobenzene-4'-sulphonic acid sodium salt, which is used without further purification in the next reaction stage.

b. 46 g of crude 3-n-decyloxy-4-hydroxy-azobenzene-4'-sulphonic acid sodium salt is heated with 4 g of powdered sodium hydroxide and 500 ml of toluene on a water separator until anhydrous solvent distills over. To the reaction mixture are then added 100 ml of dimethylformamide (anhydrous) and 0.5 g of sodium iodide, and the toluene is removed by distillation (internal temperature 130°). After the mixture has cooled to 80°, 11 g of cyclopropylmethyl chloride is added. The reaction temperature is now raised within one hour to 120°–125° and held there for a further 2 hours. After cooling, the mixture is acidified with conc. hydrochloric acid; it is then filtered to obtain, after recrystallisation of the residue from 80% ethanol, 3-n-decyloxy-4-cyclopropylmethoxy-azobenzene-4'-sulphonic acid sodium salt.

c. 26 g of 3-n-decyloxy-4-cyclopropylmethoxy-azobenzene-4'-sulphonic acid sodium salt is dissolved in 500 ml of methylcellosolve, and the solution, after addition of 6 g of Raney nickel, is hydrogenated at 20° to 40° under normal pressure, until the absorption of hydrogen ceases. Filtration is performed, the filtrate is concentrated by evaporation, the residue is treated with 2N sodium hydroxide solution and extracted with chloroform. The organic phases are dried with sodium sulphate, concentrated by evaporation and the residue is distilled. The resulting product is 3-n-decyloxy-4-cyclopropyl-methoxy-aniline, B.P. 185° C / 0.003 Torr.

What we claim is:

1. A process for the production of 3,4dialkoxyanilines of formula I

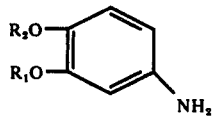 (I)

wherein (a) $R_1$ and $R_2$ are different from each other and each of $R_1$ and $R_2$ represents a member of the group consisting of $C_1$–$C_{20}$-alkyl and $C_3$–$C_6$-cycloalkyl-$C_1$–$C_4$-alkyl or (b) $R_1$ represents $C_1$–$C_4$ alkyl and $R_2$ represents $C_8$–$C_{10}$ alkyl, which comprises reacting pyrocatechol with a reactive ester of an alcohol derived from the group $R_1$, to form the corresponding pyrocatechol monoether of formula II

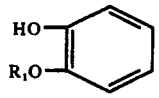 (II)

coupling this pyrocatechol monoether with a phenyl diazonium salt to give an azobenzene of formula III

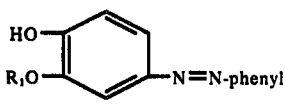 (III)

relating this azobenzene with a reactive ester of an alcohol derived from the group $R_2$, to form a 3,4-dialkoxyazobenzene of formula IV

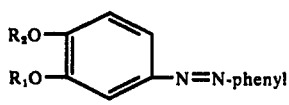 (IV)

and then reductively splitting this 3,4-dialkoxy azobenzene to a 3,4-dialkoxyaniline of formula I.

2. Process according to claim 1, wherein the reactive esters of alcohols drived from residues $R_1$ and $R_2$ employed are halides, sulphuric acid esters or sulphonic acid esters.

3. Process according to claim 1, wherein the reactive ester of an alcohol derived from the residue $R_1$ is reacted with excess pyrocatechol.

4. Process according to claim 1, wherein a phenyl diazonium salt is used which is derived from aniline, toluidine or sulphanilic acid.

5. Process according to claim 1, wherein the reductive cleavage of the azobenzene of formula IV is performed with a reducing agent selected from the group consisting of sodium dithionite, hydrogen sulphide or a salt thereof, sodium bisulphite, zinc and tin (II) chloride.

6. Process according to claim 1, wherein the reductive cleavage of the azobenzene of formula IV is performed with catalytically activated hydrogen.

7. A process according to claim 1 in which one of $R_1$ and $R_2$ is $C_8$–$C_{16}$ alkyl and the other is $C_3$–$C_6$ cycloalkyl $C_1$–$C_4$ alkyl.

8. A process according to claim 7 in which $R_1$ is n-decyl and $R_2$ is cyclopropylmethyl.

9. A process according to claim 1 in which $R_1$ is $C_1$–$C_4$ alkyl and $R_2$ is $C_8$–$C_{10}$ alkyl.

10. A process according to claim 9 in which $R_1$ is ethoxy and $R_2$ is n-decyl.

* * * * *